(12) United States Patent
Talley

(10) Patent No.: US 12,264,178 B2
(45) Date of Patent: Apr. 1, 2025

(54) URSOLIC ACID MORPHOLINE AND DIETHANOLAMINE SALTS

(71) Applicant: EMMYON, INC., Rochester, MN (US)

(72) Inventor: John J. Talley, St. Louis, MO (US)

(73) Assignee: EMMYON, INC., Rochester, MN (US)

( * ) Notice: Subject to any disclaimer, the term of this patent is extended or adjusted under 35 U.S.C. 154(b) by 0 days.

(21) Appl. No.: 18/910,781

(22) Filed: Oct. 9, 2024

(65) Prior Publication Data
US 2025/0034203 A1 Jan. 30, 2025

Related U.S. Application Data

(60) Division of application No. 16/811,730, filed on Mar. 6, 2020, which is a continuation-in-part of application No. PCT/US2018/049742, filed on Sep. 6, 2018.

(60) Provisional application No. 62/649,938, filed on Mar. 29, 2018, provisional application No. 62/558,004, filed on Sep. 13, 2017.

(51) Int. Cl.
| A61K 45/06 | (2006.01) |
| A23L 29/00 | (2016.01) |
| C07J 63/00 | (2006.01) |

(52) U.S. Cl.
CPC ............ *C07J 63/008* (2013.01); *A23L 29/03* (2016.08); *A61K 45/06* (2013.01)

(58) Field of Classification Search
None
See application file for complete search history.

(56) References Cited

U.S. PATENT DOCUMENTS

| 9,295,664 B2 | 3/2016 | Adams et al. |
| 9,856,204 B2 | 1/2018 | Adams et al. |
| 10,137,136 B2 | 11/2018 | Adams et al. |
| 2003/0153538 A1 | 8/2003 | Kuno et al. |
| 2016/0304553 A1 | 10/2016 | Baharaff et al. |
| 2017/0056414 A1 | 3/2017 | Slaga et al. |
| 2020/0207802 A1 | 7/2020 | Talley |

FOREIGN PATENT DOCUMENTS

| CN | 1450900 A | 10/2003 |
| CN | 101891795 A | 11/2010 |
| CN | 102241723 A | 11/2011 |
| CN | 102516351 A | 6/2012 |
| CN | 103037692 A | 4/2013 |
| CN | 104688745 A | 6/2015 |
| CN | 106822153 A | 6/2017 |
| EP | 1321145 A1 | 6/2003 |
| EP | 1566170 A1 | 8/2005 |
| JP | H1129467 A | 2/1999 |
| JP | 2003313774 A | 11/2003 |
| JP | 2014/507422 A | 3/2014 |
| JP | 2015/510515 A | 4/2015 |
| JP | 2015/516422 A | 6/2015 |
| KR | 20120028043 A | 3/2012 |
| WO | 2002/043736 A1 | 6/2002 |
| WO | 2002/078468 A1 | 10/2002 |
| WO | 2011115069 A1 | 9/2011 |
| WO | 2011146768 A1 | 11/2011 |
| WO | WO 2011/146768 | * 11/2011 ............. A01N 43/04 |
| WO | 2012170546 A1 | 12/2012 |
| WO | 2019055280 A1 | 3/2019 |

OTHER PUBLICATIONS

Wozniak, L., Skapska, S., and Marszalek, K. (2015) Ursolic Acid—A Pentacyclic Triterpenoid with a Wide Spectrum of Pharmacological Activities. *Molecules* 20, 20614-20641.

Liu, J. (2005) Oleanolic acid and ursolic acid: research perspectives. *J Ethnopharmacol* 100, 92-94.

Sultana, N. (2011) Clinically useful anticancer, antitumor, and antiwrinkle agent, ursolic acid and related derivatives as medicinally important natural product. *J Enzyme Inhib Med Chem* 26, 616-64.

Liu, J. (1995) Pharmacology of oleanolic acid and ursolic acid. *J Ethnopharmacol* 49, 57-68.

Shanmugam, M. K., Dai, X., Kumar, A. P., Tan, B. K., Sethi, G., and Bishayee, A. (2013) Ursolic acid in cancer prevention and treatment: molecular targets, pharmacokinetics and clinical studies. *Biochem Pharmacol* 85, 1579-1587.

Kashyap, D., Tuli, H. S., and Sharma, A. K. (2016) Ursolic acid (UA): A metabolite with promising therapeutic potential. *Life Sci* 146, 201-213.

Lopez-Hortas, L., Perez-Larran, P., Gonzalez-Munoz, M. J., Falque, E., and Dominguez, H. (2018) Recent developments on the extraction and application of ursolic acid. A review. *Food Res Int* 103, 130-149.

Pironi, A. M., de Araujo, P. R., Fernandes, M. A., Salgado, H. R. N., and Chorilli, M. (2018) Characteristics, Biological Properties and Analytical Methods of Ursolic Acid: A Review. *Crit Rev Anal Chem* 48, 86-93.

Cargnin, S. T., and Gnoatto, S. B. (2017) Ursolic acid from apple pomace and traditional plants: A valuable triterpenoid with functional properties. *Food Chem* 220, 477-489.

Lee, S. U., Park, S. J., Kwak, H. B., Oh, J., Min, Y. K., and Kim, S. H. (2008) Anabolic activity of ursolic acid in bone: Stimulating osteoblast differentiation in vitro and inducing new bone formation in vivo. *Pharmacol Res* 58, 290-296.

Lu, J., Zheng, Y. L., Wu, D. M., Luo, L., Sun, D. X., and Shan, Q. (2007) Ursolic acid ameliorates cognition deficits and attenuates oxidative damage in the brain of senescent mice induced by D-galactose. *Biochem Pharmacol* 74, 1078-1090.

Wang, X. T., Gong, Y., Zhou, B., Yang, J. J., Cheng, Y., Zhao, J. G., and Qi, M. Y. (2018) Ursolic acid ameliorates oxidative stress, inflammation and fibrosis in diabetic cardiomyopathy rats. *Biomed Pharmacother* 97, 1461-1467.

(Continued)

Primary Examiner — Craig D Ricci
(74) *Attorney, Agent, or Firm* — HESLIN ROTHENBERG FARLEY & MESITI P.C.

(57) ABSTRACT

The invention provides diethanolamine and morpholine salts of ursolic acid. Compositions containing the salts, and methods of using the salts are also provided.

34 Claims, 6 Drawing Sheets

(56) References Cited

OTHER PUBLICATIONS

Zhou, Y., Li, J. S., Zhang, X., Wu, Y. J., Huang, K., and Zheng, L. (2010) Ursolic acid inhibits early lesions of diabetic nephropathy. *Int J Mol Med* 26, 565-570.

Ling, C., Jinping, L., Xia, L., and Renyong, Y. (2013) Ursolic Acid provides kidney protection in diabetic rats. *Curr Ther Res Clin Exp* 75, 59-63.

Ding, H., Wang, H., Zhu, L., and Wei, W. (2017) Ursolic Acid Ameliorates Early Brain Injury After Experimental Traumatic Brain Injury in Mice by Activating the Nrf2 Pathway. *Neurochem Res* 42, 337-346.

Ma, J. Q., Ding, J., Zhang, L., and Liu, C. M. (2015) Protective effects of ursolic acid in an experimental model of liver fibrosis through Nrf2/ARE pathway. *Clin Res Hepatol Gastroenterol* 39, 188-197.

Zhang, T., Su, J., Wang, K., Zhu, T., and Li, X. (2014) Ursolic acid reduces oxidative stress to alleviate early brain injury following experimental subarachnoid hemorrhage. *Neurosci Lett* 579, 12-17.

Hwang, T. L., Shen, H. I., Liu, F. C., Tsai, H. I., Wu, Y. C., Chang, F. R., and Yu, H. P. (2014) Ursolic acid inhibits superoxide production in activated neutrophils and attenuates trauma-hemorrhage shock-induced organ injury in rats. *PLoS One* 9, e111365.

Martinez-Abundis, E., Mendez-Del Villar, M., Perez-Rubio, K. G., Zuniga, L. Y., Cortez-Navarrete, M., Ramirez-Rodriguez, A., and Gonzalez-Ortiz, M. (2016) Novel nutraceutic therapies for the treatment of metabolic syndrome. *World J Diabetes* 7, 142-152.

Somova, L. O., Nadar, A., Rammanan, P., and Shode, F. O. (2003) Cardiovascular, antihyperlipidemic and antioxidant effects of oleanolic and ursolic acids in experimental hypertension. *Phytomedicine* 10, 115-121.

Somova, L. I., Shode, F. O., Ramnanan, P., and Nadar, A. (2003) Antihypertensive, antiatherosclerotic and antioxidant activity of triterpenoids isolated from *Olea europaea*, subspecies *africana* leaves. *J Ethnopharmacol* 84, 299-305.

Dyle et al., "Systems-based Discovery of Tomatidine as a Natural Small Molecule Inhibitor of Skeletal Muscle Atrophy," The Journal of Biological Chemistry, vol. 289, No. 21, May 23, 2014, pp. 14913-14924.

Kunkel et al., "mRNA Expression Signatures of Human Skeletal Muscle Atrophy Identify a Natural Compound that Increases Muscle Mass," Cell Metabolism 13, Jun. 8, 2011, pp. 627-638.

Kunkel et al., "Ursolic Acid Increases Skeletal Muscle and Brown Fat and Decreases Diet-Induced Obesity, glucose Intolerance and Fatty Liver Disease," PLOS One, vol. 7, Issue 6, Jun. 2012 pp. 1-8.

International Search Report and Written Opinion of the International Searching Authority from PCT/US2018/049742, mailed Jan. 22, 2019.

Qiang LEE et al, A New Brochure of Effective Components in Traditional Chinese Medicine, Peking Union Medical College Press. Jan. 31, 2008. pp. 651-652, Abstract Only.

Qingguo Meng et al, "Research Progress in Synthesis and Activity of Ursolic Acid Derivatives". Journal of Jining Medical College, vol. 40, No. 40: Aug. 20, 2017. pp. 246-247, Abstract Only.

Fengjuan Xia et al, "Research progress of structure modification technology in domestic patents related to ursolic acid derivatives". China Medical Herald, vol. 10, No. 27, Sep. 25, 2013. pp. 33-36, Abstract Only.

\* cited by examiner

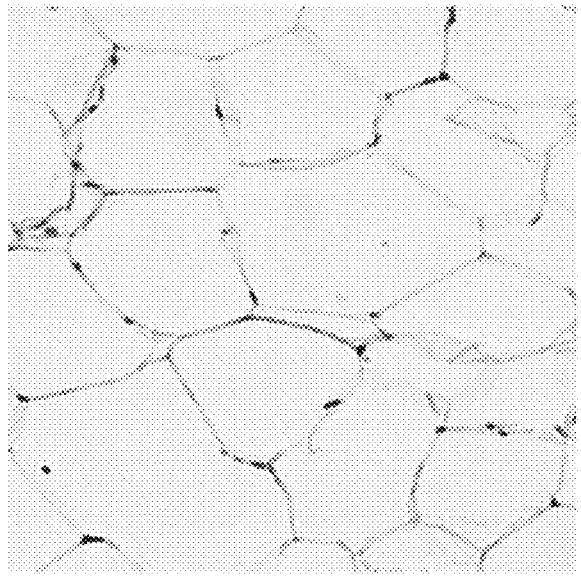
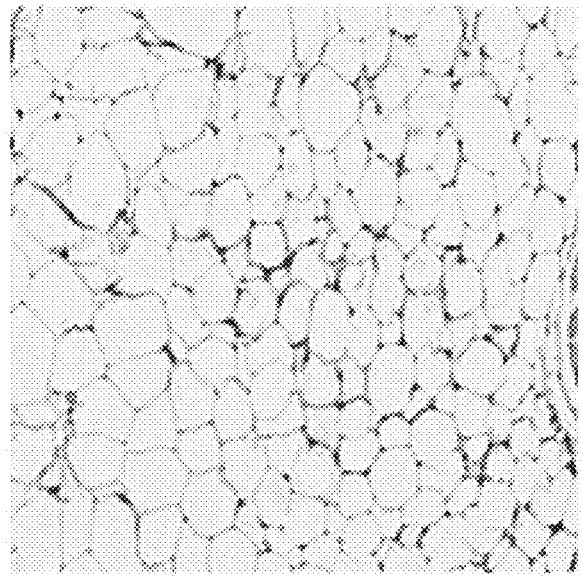
FIG. 2A
FIG. 2B

URSOLIC ACID MORPHOLINE AND DIETHANOLAMINE SALTS

CROSS REFERENCE TO RELATED APPLICATIONS

This application is a divisional application of U.S. application Ser. No. 16/811,730, filed on Mar. 6, 2020, which is a continuation-in-part application of International Application No. PCT/US2018/049742, filed Sep. 6, 2018, and published as WO 2019/055280 on Mar. 21, 2019, which claims the benefit of U.S. Provisional Application Nos. 62/558,004 (filed Sep. 13, 2017) and 62/649,938 (filed Mar. 29, 2018). The entire contents of each of the prior applications are hereby incorporated herein by reference.

FEDERALLY SPONSORED RESEARCH

This invention was made with government support under R43 AR069400 awarded by National Institutes of Health. The government has certain rights in the invention.

FIELD OF THE INVENTION

The present invention provides novel diethanolamine and morpholine salts of ursolic acid, which exhibit superior efficacy and properties. Compositions comprising the salts, and methods employing the salts are also provided.

BACKGROUND OF THE INVENTION

Ursolic acid is a pentacyclic triterpene acid. A range of biological effects of ursolic acid are discussed in WO 2011/146768 and WO 2012/170546. At the molecular level, ursolic acid inhibits the STAT3 activation pathway, reduces matrix metalloproteinase-9 expression via the glucocorticoid receptor, inhibits protein tyrosine phosphatases, acts as an insulin mimetic, activates PPARα, inhibits NF-kB transcription factors, translocates hormone-sensitive lipase to stimulate lipolysis and inhibits the hepatic polyol pathway, among other effects.

SUMMARY OF THE INVENTION

Briefly, the present invention provides novel ursolic acid diethanolamine and morpholine salts, as well as related compositions and methods. The salts exhibit superior properties, including effects on skeletal muscle, as compared to ursolic acid per se and other ursolic acid salts.

Certain embodiments of the presently-disclosed ursolic acid salts, compositions comprising the salts, and methods employing the salts have several features, no single one of which is solely responsible for their desirable attributes. Without limiting the scope of the ursolic acid salts, compositions comprising the salts, and methods employing the salts as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. For example, embodiments of the invention provide unexpectedly superior properties compared to, e.g., native ursolic acid and other ursolic acid salts, including, e.g., efficaciousness in stimulating skeletal muscle hypertrophy, increasing lean muscle mass, decreasing fat mass, increasing skeletal muscle fiber size, decreasing adipocyte size, reducing obesity and/or blood glucose, improving glucose tolerance, etc.

In a first aspect, the invention provides an ursolic acid salt selected from ursolic acid diethanolamine salt and ursolic acid morpholine salt.

In a second aspect, the invention provides a composition comprising an ursolic acid salt selected from ursolic acid diethanolamine salt and ursolic acid morpholine salt, and a further agent.

In a third aspect, the invention provides a method for:
(i) increasing skeletal muscle mass;
(ii) treating skeletal muscle atrophy;
(iii) treating sarcopenia;
(iv) treating cachexia;
(v) increasing strength;
(vi) treating weakness;
(vii) increasing exercise capacity;
(viii) treating fatigue;
(ix) promoting muscle growth;
(x) promoting normal muscle function;
(xi) improving muscle function;
(xii) promoting muscle health;
(xiii) promoting healthy aging in muscles;
(xiv) increasing energy expenditure;
(xv) increasing the ratio of skeletal muscle to fat;
(xvi) reducing fat;
(xvii) treating obesity;
(xviii) treating diabetes;
(xix) lowering blood glucose;
(xx) treating pre-diabetes;
(xxi) treating metabolic syndrome;
(xxii) treating insulin resistance;
(xxiii) reducing plasma cholesterol;
(xxiv) treating hypercholesterolemia;
(xxv) reducing plasma triglycerides;
(xxvi) treating hypertriglyceridemia;
(xxvii) promoting healthy metabolism;
(xxviii) promoting metabolic health;
(xxix) treating hypertension;
(xxx) treating atherosclerosis
(xxxi) treating myocardial ischemia;
(xxxii) treating myocardial infarction;
(xxxiii) treating cardiomyopathy;
(xxxiv) treating cardiac arrhythmia;
(xxxv) treating non-alcoholic fatty liver disease (NAFLD);
(xxxvi) treating liver fibrosis;
(xxxvii) treating liver injury;
(xxxviii) treating lung injury;
(xxxix) treating gastric ulcers;
(xl) treating nephropathy;
(xli) promoting bone formation;
(xlii) promoting normal bone structure;
(xliii) promoting bone health;
(xliv) treating osteoporosis;
(xlv) treating cerebral ischemia;
(xlvi) treating cerebral hemorrhage;
(xlvii) treating stroke;
(xlviii) treating traumatic brain injury;
(xlix) treating dementia;
(l) treating Alzheimer's disease;
(li) treating memory loss;
(lii) treating cognitive dysfunction;
(liii) promoting normal cognitive function;
(liv) treating anxiety;
(lv) treating depression;
(lvi) reducing inflammation;

(lvii) treating arthritis;
(lviii) treating skin ulcers;
(lix) treating skin wounds;
(lx) promoting wound healing;
(lxi) treating skin dryness;
(lxii) treating skin roughness;
(lxiii) treating skin scarring;
(lxiv) treating skin wrinkles;
(lxv) reducing unwanted effects of aging;
(lxvi) treating cancer;
(lxvii) reducing tumor growth;
(lxviii) treating tumor metastasis;
(lxix) treating tumor angiogenesis;
(lxx) increasing tumor cell apoptosis;
(lxxi) decreasing protein oxidation;
(lxxii) decreasing lipid oxidation;
(lxxiii) decreasing DNA oxidation;
(lxxiv) decreasing RNA oxidation;
(lxxv) decreasing oxidation of cellular molecules;
(lxxvi) decreasing DNA damage;
(lxxvii) treating bacterial infection;
(lxxviii) reducing bacterial growth;
(lxxix) treating fungal infection;
(lxxx) reducing fungal growth;
(lxxxi) treating viral infection;
(lxxxii) treating protozoal infection;
(lxxxiii) treating nematode infection; or
(lxxxiv) treating a disease state, condition, or disorder mediated by activating transcription factor 4 (ATF4),
in a subject, the method comprising administering to the subject an ursolic acid salt selected from ursolic acid diethanolamine salt and ursolic acid morpholine salt, or a composition comprising the ursolic acid salt.

These and other features and advantages of this invention will become apparent from the following detailed description of the various aspects of the invention taken in conjunction with the appended claims and the accompanying drawings.

BRIEF DESCRIPTION OF THE DRAWINGS

The present invention will hereinafter be described in conjunction with the following drawing figures, and:

FIGS. 2A and 2B are photomicrographs of adipocytes from retroperitoneal fat pads from control and test mice, respectively, after 7 weeks of ad libitum access to either standard chow (control) or standard chow supplemented with 0.059% ursolic acid-morpholine salt.

DETAILED DESCRIPTION OF THE INVENTION

Figure 1A:
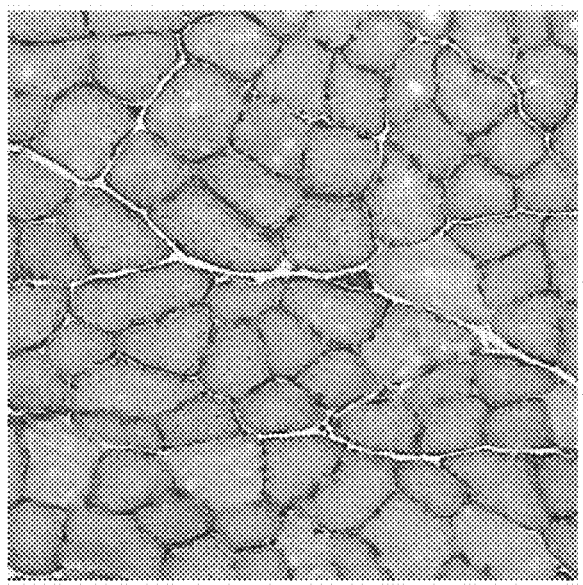
FIGS. 1A and 1B are photomicrographs of quadriceps skeletal muscle fibers from control and test mice, respectively, after 7 weeks of ad libitum access to either standard chow (control) or standard chow supplemented with 0.059% ursolic acid-morpholine salt.

Aspects of the present invention and certain features, advantages, and details thereof, are explained more fully below. Descriptions of well-known materials, equipment, processing techniques, etc., are omitted so as to not unnecessarily obscure the invention in detail.

In a first aspect, the invention provides an ursolic acid salt selected from ursolic acid diethanolamine salt and ursolic acid morpholine salt.

The inventive ursolic acid salts can be synthesized by techniques known in the art. The starting materials of the compounds of this invention are available from commercial sources or can themselves be synthesized using reagents and techniques known in the art. Non-limiting synthesis embodiments are described herein.

Ursolic acid, which has the formula

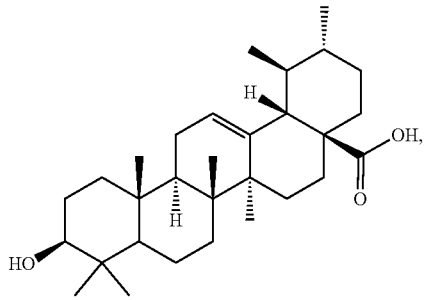

is commercially available, and is present in various plants from which it can be extracted, including apples, basil, bilberries, cranberries, elder flower, peppermint, rosemary, lavender, oregano, thyme, hawthorn, and prunes.

In some embodiments, the inventive ursolic acid salt is ursolic acid diethanolamine salt of formula

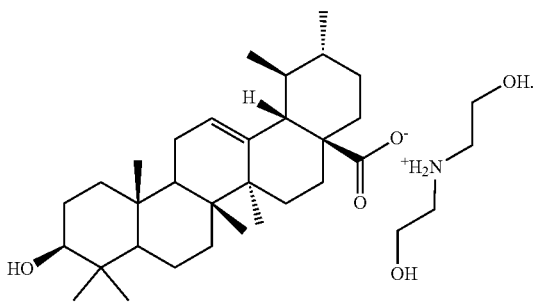 [SMILES: C[C@H]1[C@H](C)CC[C@]2(C(=O)[O-])CC[C@]3(C)C(=CCC4[C@@]5(C)CC[C@H](O)C(C)(C)C5CC[C@]43C)[C@H]12 ; OCC[NH2+]CCO]

In some embodiments, the inventive ursolic acid salt is ursolic acid morpholine salt of formula

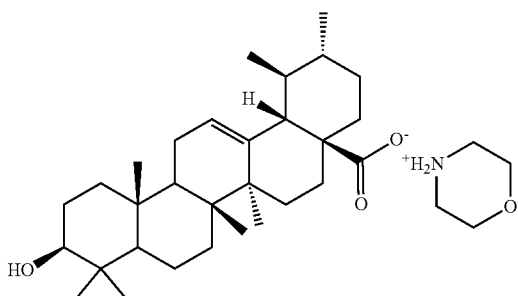

In a second aspect, the invention provides a composition comprising an ursolic acid salt selected from ursolic acid diethanolamine salt and ursolic acid morpholine salt, and a further agent.

The further agent is a component, in addition to the ursolic acid salt, that is present in the composition. Persons having ordinary skill in the art are familiar with various types of further agents that may be included in a composition. For example, in some non-limiting embodiments, the further agent comprises an excipient, binder, diluent, carrier, other delivery vehicle or system, filler, salt, buffer, preservative, antioxidant, stabilizer, sweetening agent, or flavor agent.

In some embodiments, the further agent is a physiologically acceptable agent. As used herein, a physiologically acceptable agent is an agent that does not show significant toxicity to an intended subject at the dose of administration. The term physiologically acceptable agent comprises generally regarded as safe (GRAS) substances. GRAS substances are listed by the Food and Drug Administration in the Code of Federal Regulations (CFR) at 21 CFR. § 182 and 21 CFR § 184. The August 2017 versions of 21 CFR. § 182 and 21 CFR § 184 are hereby incorporated herein by reference. The term physiologically acceptable agent also comprises pharmaceutically acceptable agents.

The term "pharmaceutically acceptable," as used herein, refers to a component that is, within the scope of sound medical judgment, suitable for use in contact with the tissues of a subject (e.g., human or other animal) without undue toxicity, irritation, allergic response and the like, and is commensurate with a reasonable benefit/risk ratio.

In some embodiments, the inventive composition is formulated for pharmaceutical use (i.e., is "a pharmaceutical composition"). Pharmaceutical compositions comprise a pharmaceutically acceptable carrier, adjuvant, or vehicle that is "acceptable" in the sense of being compatible with the other ingredients of the formulation and not deleterious to the recipient thereof in amounts typically used in medicaments.

Pharmaceutically acceptable carriers, adjuvants and vehicles that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the composition is a pharmaceutical composition, nutraceutical composition, food composition, or dietary supplement.

In some embodiments, the composition is in the form of, or comprises a non-naturally occurring oral delivery vehicle. Such delivery vehicles exclude naturally occurring vehicles such as plants and fruits. Oral delivery vehicles include, but are not limited to capsules, pills, tablets, cachets, syrups, foods, and beverages.

In some embodiments, the composition is in the form of one or more tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a subject.

In a third aspect, the invention provides a method for:
(i) increasing skeletal muscle mass;
(ii) treating skeletal muscle atrophy;
(iii) treating sarcopenia;
(iv) treating cachexia;
(v) increasing strength;
(vi) treating weakness;
(vii) increasing exercise capacity;
(viii) treating fatigue;
(ix) promoting muscle growth;
(x) promoting normal muscle function;
(xi) improving muscle function;
(xii) promoting muscle health;
(xiii) promoting healthy aging in muscles;
(xiv) increasing energy expenditure;
(xv) increasing the ratio of skeletal muscle to fat;
(xvi) reducing fat;
(xvii) treating obesity;
(xviii) treating diabetes;
(xix) lowering blood glucose;
(xx) treating pre-diabetes;
(xxi) treating metabolic syndrome;
(xxii) treating insulin resistance;
(xxiii) reducing plasma cholesterol;
(xxiv) treating hypercholesterolemia;
(xxv) reducing plasma triglycerides;
(xxvi) treating hypertriglyceridemia;
(xxvii) promoting healthy metabolism;
(xxviii) promoting metabolic health;
(xxix) treating hypertension;
(xxx) treating atherosclerosis
(xxxi) treating myocardial ischemia;
(xxxii) treating myocardial infarction;
(xxxiii) treating cardiomyopathy;
(xxxiv) treating cardiac arrhythmia;
(xxxv) treating non-alcoholic fatty liver disease (NAFLD);
(xxxvi) treating liver fibrosis;
(xxxvii) treating liver injury;
(xxxviii) treating lung injury;
(xxxix) treating gastric ulcers;
(xl) treating nephropathy;
(xli) promoting bone formation;
(xlii) promoting normal bone structure;
(xliii) promoting bone health;
(xliv) treating osteoporosis;
(xlv) treating cerebral ischemia;
(xlvi) treating cerebral hemorrhage;
(xlvii) treating stroke;
(xlviii) treating traumatic brain injury;
(xlix) treating dementia;
(l) treating Alzheimer's disease;
(li) treating memory loss;
(lii) treating cognitive dysfunction;
(liii) promoting normal cognitive function;
(liv) treating anxiety;
(lv) treating depression;
(lvi) reducing inflammation;

(lvii) treating arthritis;
(lviii) treating skin ulcers;
(lix) treating skin wounds;
(lx) promoting wound healing;
(lxi) treating skin dryness;
(lxii) treating skin roughness;
(lxiii) treating skin scarring;
(lxiv) treating skin wrinkles;
(lxv) reducing unwanted effects of aging;
(lxvi) treating cancer;
(lxvii) reducing tumor growth;
(lxviii) treating tumor metastasis;
(lxix) treating tumor angiogenesis;
(lxx) increasing tumor cell apoptosis;
(lxxi) decreasing protein oxidation;
(lxxii) decreasing lipid oxidation;
(lxxiii) decreasing DNA oxidation;
(lxxiv) decreasing RNA oxidation;
(lxxv) decreasing oxidation of cellular molecules;
(lxxvi) decreasing DNA damage;
(lxxvii) treating bacterial infection;
(lxxviii) reducing bacterial growth;
(lxxix) treating fungal infection;
(lxxx) reducing fungal growth;
(lxxxi) treating viral infection;
(lxxxii) treating protozoal infection;
(lxxxiii) treating nematode infection; or
(lxxxiv) treating a disease state, condition, or disorder mediated by activating transcription factor 4 (ATF4), in a subject, the method comprising administering to the subject an effective amount of an ursolic acid salt selected from ursolic acid diethanolamine salt and ursolic acid morpholine salt, or a composition comprising the ursolic acid salt.

Various uses as described in the foregoing paragraph are described relative to ursolic acid per se in the following references, the disclosures of which are hereby incorporated by reference herein in their entirety:

1. Wozniak, L., Skapska, S., and Marszalek, K. (2015) Ursolic Acid—A Pentacyclic Triterpenoid with a Wide Spectrum of Pharmacological Activities. *Molecules* 20, 20614-20641
2. Liu, J. (2005) Oleanolic acid and ursolic acid: research perspectives. *J Ethnopharmacol* 100, 92-94
3. Sultana, N. (2011) Clinically useful anticancer, antitumor, and antiwrinkle agent, ursolic acid and related derivatives as medicinally important natural product. *J Enzyme Inhib Med Chem* 26, 616-642
4. Liu, J. (1995) Pharmacology of oleanolic acid and ursolic acid. *J Ethnopharmacol* 49, 57-68
5. Shanmugam, M. K., Dai, X., Kumar, A. P., Tan, B. K., Sethi, G., and Bishayee, A. (2013) Ursolic acid in cancer prevention and treatment: molecular targets, pharmacokinetics and clinical studies. *Biochem Pharmacol* 85, 1579-1587
6. Kashyap, D., Tuli, H. S., and Sharma, A. K. (2016) Ursolic acid (UA): A metabolite with promising therapeutic potential. *Life Sci* 146, 201-213
7. Lopez-Hortas, L., Perez-Larran, P., Gonzalez-Munoz, M. J., Falque, E., and Dominguez, H. (2018) Recent developments on the extraction and application of ursolic acid. A review. *Food Res Int* 103, 130-149
8. Pironi, A. M., de Araujo, P. R., Fernandes, M. A., Salgado, H. R. N., and Chorilli, M. (2018) Characteristics, Biological Properties and Analytical Methods of Ursolic Acid: A Review. *Crit Rev Anal Chem* 48, 86-93
9. Cargnin, S. T., and Gnoatto, S. B. (2017) Ursolic acid from apple pomace and traditional plants: A valuable triterpenoid with functional properties. *Food Chem* 220, 477-489
10. Lee, S. U., Park, S. J., Kwak, H. B., Oh, J., Min, Y. K., and Kim, S. H. (2008) Anabolic activity of ursolic acid in bone: Stimulating osteoblast differentiation in vitro and inducing new bone formation in vivo. *Pharmacol Res* 58, 290-296
11. Lu, J., Zheng, Y. L., Wu, D. M., Luo, L., Sun, D. X., and Shan, Q. (2007) Ursolic acid ameliorates cognition deficits and attenuates oxidative damage in the brain of senescent mice induced by D-galactose. *Biochem Pharmacol* 74, 1078-1090
12. Wang, X. T., Gong, Y., Zhou, B., Yang, J. J., Cheng, Y., Zhao, J. G., and Qi, M. Y. (2018) Ursolic acid ameliorates oxidative stress, inflammation and fibrosis in diabetic cardiomyopathy rats. *Biomed Pharmacother* 97, 1461-1467
13. Zhou, Y., Li, J. S., Zhang, X., Wu, Y. J., Huang, K., and Zheng, L. (2010) Ursolic acid inhibits early lesions of diabetic nephropathy. *Int J Mol Med* 26, 565-570
14. Ling, C., Jinping, L., Xia, L., and Renyong, Y. (2013) Ursolic Acid provides kidney protection in diabetic rats. *Curr Ther Res Clin Exp* 75, 59-63
15. Ding, H., Wang, H., Zhu, L., and Wei, W. (2017) Ursolic Acid Ameliorates Early Brain Injury After Experimental Traumatic Brain Injury in Mice by Activating the Nrf2 Pathway. *Neurochem Res* 42, 337-346
16. Ma, J. Q., Ding, J., Zhang, L., and Liu, C. M. (2015) Protective effects of ursolic acid in an experimental model of liver fibrosis through Nrf2/ARE pathway. *Clin Res Hepatol Gastroenterol* 39, 188-197
17. Zhang, T., Su, J., Wang, K., Zhu, T., and Li, X. (2014) Ursolic acid reduces oxidative stress to alleviate early brain injury following experimental subarachnoid hemorrhage. *Neurosci Lett* 579, 12-17
18. Hwang, T. L., Shen, H. I., Liu, F. C., Tsai, H. I., Wu, Y. C., Chang, F. R., and Yu, H. P. (2014) Ursolic acid inhibits superoxide production in activated neutrophils and attenuates trauma-hemorrhage shock-induced organ injury in rats. *PLoS One* 9, e111365
19. Martinez-Abundis, E., Mendez-Del Villar, M., Perez-Rubio, K. G., Zuniga, L. Y., Cortez-Navarrete, M., Ramirez-Rodriguez, A., and Gonzalez-Ortiz, M. (2016) Novel nutraceutic therapies for the treatment of metabolic syndrome. *World J Diabetes* 7, 142-152
20. Somova, L. O., Nadar, A., Rammanan, P., and Shode, F. O. (2003) Cardiovascular, antihyperlipidemic and antioxidant effects of oleanolic and ursolic acids in experimental hypertension. *Phytomedicine* 10, 115-121
21. Somova, L. I., Shode, F. O., Ramnanan, P., and Nadar, A. (2003) Antihypertensive, antiatherosclerotic and antioxidant activity of triterpenoids isolated from *Olea europaea*, subspecies *africana* leaves. *J Ethnopharmacol* 84, 299-305

In some embodiments, the ursolic acid salts described herein are useful for, inter alia, the same indications as ursolic acid per se.

As used herein, the term "subject" refers to an animal that is the target of administration. In some embodiments, the subject is a human. In other embodiments, the subject is a non-human animal. In some embodiments, the subject is a non-rodent animal. In some embodiments, the subject is a non-human, and/or non-rodent animal. In some embodiments, the subject is a vertebrate and/or an amphibian. In some embodiments, the subject is a human, non-human primate, horse, pig, rabbit, dog, sheep, goat, cow, cat, guinea pig, hamster, ferret, fish, bird, or rodent. In some embodiments, the subject is a human or a domesticated animal. In some embodiments, the subject is a domesticated animal, such as a domesticated fish, domesticated crustacean, or domesticated mollusk. In some embodiments, the domesticated animal is poultry. In some embodiments, the poultry is selected from chicken, turkey, duck, and goose. In some embodiments, the domesticated animal is livestock. In some embodiments, the livestock animal is selected from a pig, cow, horse, goat, bison, and sheep. In some embodiments, the domestic animal includes rodents. In other embodiments, the domestic animal excludes some or all rodents. In some embodiments, the domestic animal excludes mice and rats.

As used herein, the term "treatment" and various forms thereof (e.g., "treating") refer to the management (e.g., medical management) of a patient/subject with the intent to cure, ameliorate, stabilize, or forestall a disease, pathological condition, or disorder. The term includes administering an inventive compound and/or composition to a subject with the purpose to cure, heal, alleviate, relieve, alter, remedy, ameliorate, improve, or affect a disease state, condition, or disorder, the symptoms of the disease state, condition, or disorder or the predisposition toward the disease state, condition, or disorder. The term "treatment" and various forms thereof include the use for aesthetic and self-improvement purposes. For example, such uses include, but are not limited to, the administration of the disclosed compound in nutraceuticals, medicinal food, energy bar, energy drink, supplements (such as multivitamins). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various embodiments, the term covers any treatment of a subject, and includes: (i) impeding the disease from occurring in a subject that can be predisposed to the disease but has not yet been diagnosed as having it; (ii) inhibiting the disease, i.e., arresting its development; or (iii) relieving the disease, i.e., causing regression of the disease. The term additionally includes forestalling or impeding the onset, recurrence or intensification of a disease state, condition, or disorder disclosed herein, and ameliorating and/or reducing the occurrence of symptoms of a disease state, condition, or disorder.

Embodiments of the methods of treatment and uses of the inventive ursolic acid salts typically comprise administering an effective amount (e.g., a therapeutically effective amount) of the salt to a subject in need thereof. As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount can vary depending on the compound, the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. A subject in need of treatment includes a subject that is at risk of needing the treatment. As used herein, an "at risk" subject is one that is at risk of developing a condition or disorder to be treated. This may be shown, for example, by one or more risk factors, which are measurable parameters that correlate with development of a condition or disorder and are known in the art.

In some embodiments, the subject has been identified to be in need of treatment for a condition or disorder, or has been diagnosed with a condition or disorder prior to administering an inventive salt to the subject. In some embodiments, the subject has not been diagnosed with a condition or disorder prior to administering an inventive salt to the subject. In some embodiments, the subject has not been diagnosed with cancer or diabetes. In other embodiments, the subject may have been diagnosed with a condition or disorder such as cancer or diabetes.

As used herein, the term "diagnosed" means having been subjected to a physical examination by a person of skill, for example, a physician, and found to have a condition that can be diagnosed or treated by the inventive ursolic acid salts, compositions, or methods/uses disclosed herein. For example, "diagnosed with a muscle atrophy disorder" means having been subjected to a physical examination by a person of skill, for example, a physician, and found to have a condition that can be diagnosed or treated by a compound or composition that can promote muscle health, promote normal muscle function, and/or promote healthy aging muscles. As a further example, "diagnosed with a need for promoting muscle health" refers to having been subjected to a physical examination by a person of skill, for example, a physician, and found to have a condition characterized by muscle atrophy or other disease wherein promoting muscle health, promoting normal muscle function, and/or promoting healthy aging muscles would be beneficial to the subject. Such a diagnosis can be in reference to a disorder, such as muscle atrophy, and the like, as discussed herein.

As used herein, the phrase "identified to be in need of treatment for a condition or disorder," or the like, refers to selection of a subject based upon need for treatment of the disorder. For example, a subject can be identified as having a need for treatment of a disorder (e.g., a disorder related to muscle atrophy) based upon an earlier diagnosis by a person of skill and thereafter subjected to treatment for the disorder. As another example, subjects intended for consumption (e.g., fish, production livestock, etc.) may be identified to be in need of treatment for, e.g., increasing muscle mass, in order to increase the average amount of meat that can be obtained per animal.

In some embodiments, the inventive ursolic acid salts are administered in a dosage ranging from about 0.001 to about 500 mg/kg of subject body weight (e.g., 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 mg/kg), including any and all ranges and subranges therein (e.g., 0.001 to 100 mg/kg, 0.01 to 75 mg/kg, 0.05 to 20 mg/kg, 0.1 to 10 mg/kg, etc.).

In some embodiments, the inventive ursolic acid salts are administered in an amount of 1 to 2,000 mg (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, or 2000 mg), including any and all ranges and subranges therein (e.g., 20 to 1900 mg, 50 to 1800 mg, 75 to 1700 mg, 100 to 1600 mg, etc.). Thus, in some embodiments where the ursolic acid salt is administered in a composition, the composition will contain such amount of the compound.

In some embodiments, the ursolic acid salt is administered in an amount that is greater than 50, 75, 100, 150, 200, 250, 300, 400, 500, 600, 750, 800, 900, 1000, 1100, 1200, 1300, 1400, or 1500 mg.

EXAMPLES

The invention will now be illustrated, but not limited, by reference to the specific embodiments described in the following examples.

Sample Preparation—Ursolic Acid Diethanolamine Salt

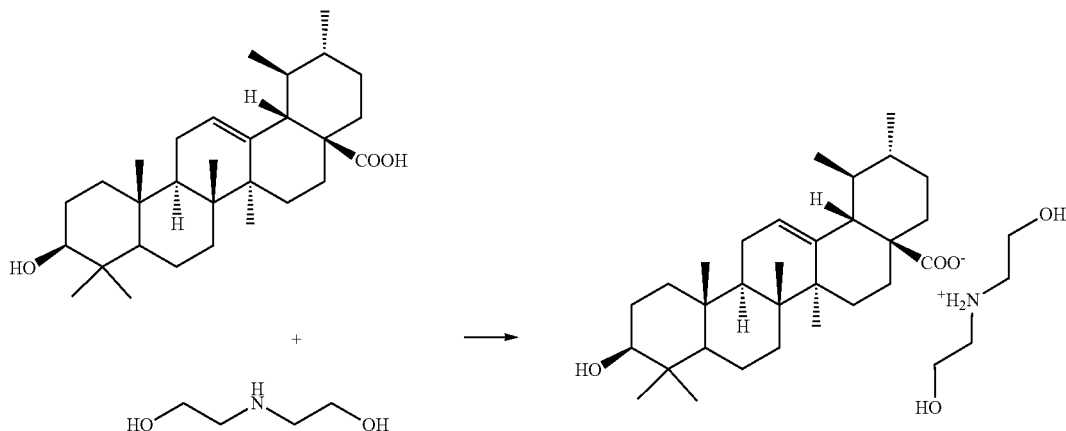

Ursolic acid (1.0450 g) and diethanolamine (208.6 mg) were dissolved in THF:MeOH (10:1) and allowed to stand, then concentrated and dried to yield a white solid, the diethanolamine salt of ursolic acid (965.0 mg). This product was used as the ursolic acid diethanolamine salt in the testing described below.

Sample Preparation—Ursolic Acid Morpholine Salt

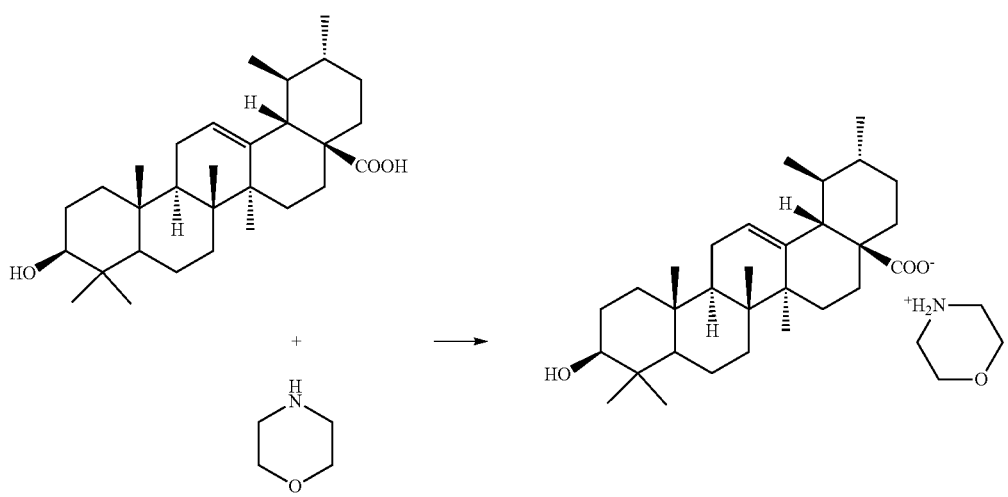

Ursolic acid (1.0715 g) was dissolved in 20 mL of THF. Morpholine (224 mg) was added, and stirred for 1.5 hours. 8 mL of hexanes was added and the homogeneous solution became cloudy. The salt was stirred at room temperature for 12 hours. No significant amount of the salt had formed. The solution was concentrated in vacuo, and the stirred residue gave a white powder that was isolated by filtration and dried in vacuo to give the morpholine salt of ursolic acid (867.1 mg). This product was used as the ursolic acid morpholine salt in the testing described below.

Comparative Grip Strength Testing for Ursolic Acid and Salts Thereof

Weight-matched cohorts of 8-week old male C57BL/6 mice were randomized to receive ad libitum access to either standard chow (control) or standard chow supplemented with either 0.050% ursolic acid, 0.200% ursolic acid, or one of the indicated ursolic acid salts: ursolic acid-ethanolamine salt; ursolic acid-tris(hydroxymethyl)aminomethane salt, hereinafter referred to as ursolic acid-"tris" salt; ursolic acid-lysine salt; ursolic acid-diethanolamine salt; ursolic acid-morpholine salt; or ursolic acid-piperazine salt. The ursolic acid-diethanolamine salt and ursolic acid-morpholine salt were prepared as described above. Ursolic acid was commercially obtained, and was used as a starting material to make the other ursolic acid salts according to techniques analogous to those above and known in the art. The doses of ursolic acid salts were molar-matched to either 0.050% ursolic acid (i.e. 0.057% ursolic acid-ethanolamine salt, 0.063% ursolic acid-tris salt, 0.066% ursolic acid-lysine salt, 0.059% ursolic acid-morpholine salt, and 0.059% ursolic acid-piperazine salt) or to 0.048% ursolic acid (i.e. 0.060% ursolic acid-diethanolamine salt). After mice had consumed these diets for 6 weeks, in vivo grip strength was measured. The results are shown below in Table I. Data are means±SEM from 12 mice per cohort. **$P<0.01$ by one-way ANOVA with Dunnett's post test.

TABLE I

| Diet | Grip Strength (% Change vs. Control) |
|---|---|
| Control | 0.0 ± 1.9 |
| 0.050% Ursolic Acid | 7.7 ± 1.9 |
| 0.200% Ursolic Acid | 9.9 ± 2.2** |
| 0.057% Ursolic Acid-Ethanolamine Salt | 2.8 ± 1.6 |
| 0.063% Ursolic Acid-Tris Salt | 5.2 ± 1.6 |
| 0.066% Ursolic Acid-Lysine Salt | 7.2 ± 2.3 |
| 0.060% Ursolic Acid-Diethanolamine Salt | 11.7 ± 2.5** |
| 0.059% Ursolic Acid-Morpholine Salt | 11.3 ± 2.1** |
| 0.059% Ursolic Acid-Piperazine Salt | 3.7 ± 2.5 |

As evidenced by the data from Table I, not all salts of ursolic acid exhibit statistically significant improvement in strength. Indeed, many may be less efficacious than the free acid at the same dose. Ursolic acid-diethanolamine salt and ursolic acid-morpholine salt were unexpectedly more potent and efficacious than native ursolic acid and other ursolic acid salts.

Ursolic Acid-Morpholine Salt—Grip Strength, Body Weight and Composition, and Skeletal Muscle Fiber Testing Weight-matched cohorts of 8-week old male C57BL/6 mice were randomized to receive ad libitum access to either standard chow (control) or standard chow supplemented with 0.059% ursolic acid-morpholine salt. After mice had consumed these diets for 7 weeks, in vivo, grip strength was measured, mice were weighed, body composition was assessed by NMR, and quadriceps muscles were dissected for histological analysis of skeletal muscle fiber cross-sectional diameter. The results are shown below in Table II. Body weight data, grip strength data, and NMR data (lean mass, fat mass, % lean and % fat) are means±SEM from 14-15 mice per cohort. Muscle fiber diameter data are means±SEM from >4200 muscle fibers per diet. *P<0.05; P<0.01; *P<0.001

TABLE II

| | Control | Ursolic Acid-Morpholine Salt |
|---|---|---|
| Initial Body Wt (g) | 26.1 ± 0.4 | 26.3 ± 0.3 |
| Final Grip Strength (g) | 165.5 ± 3.3 | 181.9 ± 2.4*** |
| Final Body Wt (g) | 35.6 ± 0.8 | 34.6 ± 1.0 |
| Final Lean Mass (g) | 19.6 ± 0.3 | 20.8 ± 0.3** |
| Final Fat Mass (g) | 10.2 ± 0.9 | 7.8 ± 1.2 |
| Final % Lean | 55.3 ± 1.4 | 61.0 ± 2.2* |
| Final % Fat | 28.0 ± 2.1 | 21.4 ± 2.9* |
| Muscle fiber diameter (μm) | 39.7 ± 0.1 | 44.8 ± 0.2*** |

The data in Table II demonstrate that ursolic acid-morpholine salt stimulated skeletal muscle hypertrophy, increased lean mass and decreased fat mass.

Ursolic Acid-Morpholine Salt—Skeletal Muscle Fiber Size Testing

Figure 1B:
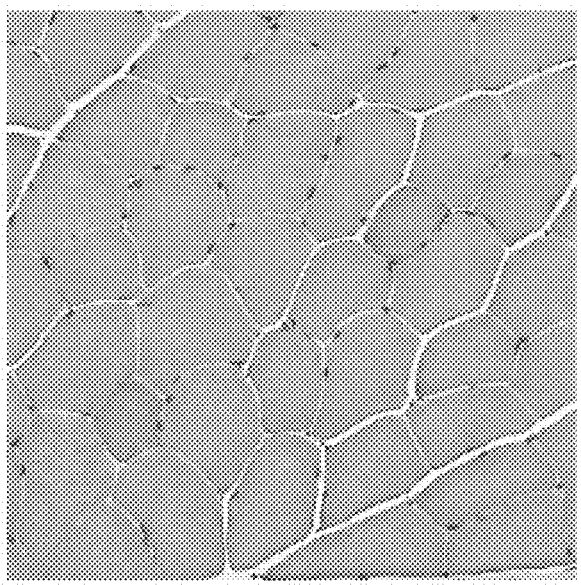

Weight-matched cohorts of 8-week old male C57BL/6 mice were randomized to receive ad libitum access to either standard chow (control) or standard chow supplemented with 0.059% ursolic acid-morpholine salt. After mice had consumed these diets for 7 weeks, quadriceps muscles were dissected, fixed, cross-sectioned, stained with hematoxylin and eosin, and subjected to photomicrography. FIG. 1A is a photomicrograph of quadriceps skeletal muscle fibers from the control group. FIG. 1B is a photomicrograph of quadriceps skeletal muscle fibers from the ursolic acid-morpholine salt group. A comparison of FIGS. 1A and 1B shows that ursolic acid-morpholine salt increased skeletal muscle fiber size.

Ursolic Acid-Morpholine Salt—Adipocyte Size Testing

Weight-matched cohorts of 8-week old male C57BL/6 mice were randomized to receive ad libitum access to either standard chow (control) or standard chow supplemented with 0.059% ursolic acid-morpholine salt. After mice had consumed these diets for 7 weeks, retroperitoneal fat pads were dissected, fixed, cross-sectioned, stained with hematoxylin and eosin, and subjected to photomicrography. FIG. 2A is a photomicrograph of adipocytes from retroperitoneal fat pads from the control group. FIG. 2B is a photomicrograph of adipocytes from retroperitoneal fat pads from the ursolic acid-morpholine salt group. A comparison of FIGS. 2A and 2B shows that ursolic acid-morpholine salt decreased adipocyte size.

Ursolic Acid-Morpholine Salt—Obesity and Blood Glucose Testing

Weight-matched cohorts of 8-week old male C57BL/6 mice were randomized to receive ad libitum access to either high-fat chow (control) or high-fat chow supplemented with 0.059% ursolic acid-morpholine salt. Just prior to starting these diets, mice were weighed and subjected to body composition analysis by NMR. After mice had consumed the diets for 9 weeks, body weight and body composition were re-assessed, retroperitoneal and epididymal fat pads were dissected and weighed, and non-fasting blood glucose was measured. The results are shown below in Table III. Data are means±SEM from 15 mice per cohort. *P<0.05; **P<0.01.

TABLE III

| | Control | Ursolic Acid-Morpholine Salt |
|---|---|---|
| Initial Body Wt (g) | 24.0 ± 0.5 | 23.8 ± 0.4 |
| Initial Lean Mass (g) | 16.5 ± 0.4 | 16.7 ± 0.4 |
| Initial Fat Mass (g) | 2.0 ± 0.2 | 1.7 ± 0.2 |
| Initial % Lean | 68.7 ± 0.8 | 70.0 ± 0.7 |
| Initial % Fat | 8.4 ± 0.9 | 7.4 ± 0.8 |
| Final Body Wt (g) | 41.6 ± 1.0 | 38.9 ± 1.2* |
| Final Lean Mass (g) | 20.3 ± 0.6 | 21.3 ± 0.6 |
| Final Fat Mass (g) | 16.5 ± 0.9 | 12.8 ± 1.4* |
| Final % Lean | 49.0 ± 1.1 | 55.3 ± 2.4* |
| Final % Fat | 39.4 ± 1.6 | 31.8 ± 3.1* |
| Retroperitoneal Fat Pad Wt (mg) | 929.4 ± 52.0 | 731.8 ± 86.9* |
| Epididymal Fat Pad Wt (mg) | 2257.0 ± 84.6 | 1804.0 ± 161.5** |
| Blood Glucose (mg/dL) | 198.1 ± 6.1 | 177.7 ± 9.9* |

The data in Table III demonstrate, inter alia, that ursolic acid-morpholine salt reduced obesity in diet-induced obese mice.

Ursolic Acid-Morpholine Salt—Glucose Tolerance Testing

Figure 3:
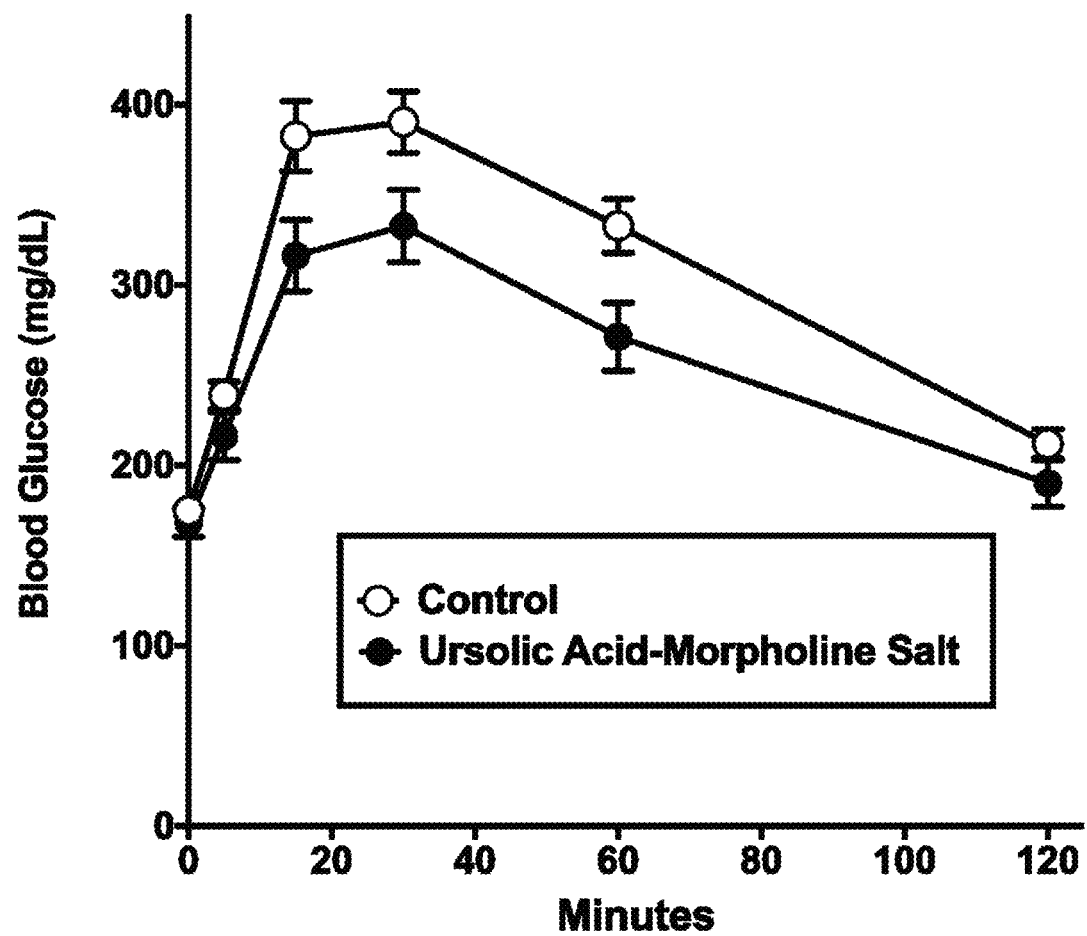
FIG. 3 is a chart depicting glucose tolerance testing results from control and test mice after 8 weeks of ad libitum access to either high-fat chow (control) or high-fat chow supplemented with 0.059% ursolic acid-morpholine salt.

Weight-matched cohorts of 8-week old male C57BL/6 mice were randomized to receive ad libitum access to either high-fat chow (control) or high-fat chow supplemented with 0.059% ursolic acid-morpholine salt. After mice had consumed the diets for 8 weeks, mice were fasted for 6 hours and then subjected to glucose tolerance testing. Results are shown in FIG. 3, which is a graph depicting glucose tolerance testing results. Data are means±SEM from 15 mice per cohort. As evident from FIG. 3, the area under the curve (AUC) for mice treated with ursolic acid-morpholine salt (31,383±1,869) is significantly lower than the AUC for control mice (37,122±1,339; P<0.01), indicating that ursolic acid-morpholine salt significantly improved glucose tolerance (i.e. reduced glucose intolerance).

Ursolic Acid-Diethanolamine Salt—Body Weight and Composition Testing

Weight-matched cohorts of 8-week old male C57BL/6 mice were randomized to receive ad libitum access to either standard chow (control), standard chow supplemented with 0.060% ursolic acid-diethanolamine salt, or standard chow supplemented with 0.180% ursolic acid-diethanolamine salt. After mice had consumed these diets for 7 weeks, mice were weighed and body composition was assessed by NMR. Results are shown below in Table IV. Data are means±SEM from 15 mice per cohort. *P<0.05.

TABLE IV

|  | Control | 0.060% Ursolic Acid-Diethanolamine Salt | 0.180% Ursolic Acid-Diethanolamine Salt |
| --- | --- | --- | --- |
| Initial Body Wt (g) | 22.8 ± 0.3 | 23.0 ± 0.3 | 22.8 ± 0.3 |
| Final Body Wt (g) | 31.8 ± 0.9 | 31.7 ± 0.5 | 30.7 ± 0.5 |
| Final Lean Mass (g) | 19.3 ± 0.3 | 20.3 ± 0.4* | 20.0 ± 0.3 |
| Final Fat Mass (g) | 7.1 ± 1.0 | 5.3 ± 0.7 | 4.4 ± 0.6* |
| Final % Lean | 61.2 ± 2.0 | 64.2 ± 1.6 | 65.5 ± 1.4* |
| Final % Fat | 21.4 ± 2.5 | 16.6 ± 2.0 | 14.1 ± 1.8* |

The Table IV data establish that ursolic acid-diethanolamine salt increased lean mass and decreased fat mass.

Direct Comparison of Ursolic Acid-Morpholine Salt to a Molar-Matched Dose of Ursolic Acid in Diet-Induced Obesity Weight-matched cohorts of 8-week old male C57BL/6 mice were randomized to receive ad libitum access to either high-fat chow (control), high-fat chow supplemented with 0.050% ursolic acid, or high-fat chow supplemented with a molar-matched dose of ursolic acid-morpholine salt (0.059%). Just prior to starting these diets, mice were weighed and subjected to body composition analysis by NMR. After mice had consumed the diets for 8 weeks, body weight and body composition were re-assessed, retroperitoneal and epididymal fat pads were dissected and weighed, and skeletal muscles (tibialis anterior, gastrocnemius, soleus, quadriceps and triceps) were dissected and weighed. In each mouse, the total dissected skeletal muscle weight (combined weight of bilateral tibialis anterior, gastrocnemius, soleus, quadriceps and triceps muscles) was normalized to the final body weight. Data are means±SEM from 10 mice per cohort. Different letters denote statistically significant differences (P<0.05 by one-way ANOVA with Tukey's post test). Results are summarized in Table V.

TABLE V

|  | Control | 0500.% Ursolic Acid | 0.059% Ursolic Acid-Morpholine Salt |
| --- | --- | --- | --- |
| Initial Body Wt (g) | 23.4 ± 0.3 [a] | 23.2 ± 0.3 [a] | 23.4 ± 0.6 [a] |
| Initial Lean Mass (g) | 16.0 ± 0.3 [a] | 15.9 ± 0.4 [a] | 15.9 ± 0.5 [a] |
| Initial Fat Mass (g) | 1.6 ± 0.2 [a] | 1.2 ± 0.1 [a] | 1.3 ± 0.1 [a] |
| Initial % Lean | 68.1 ± 0.6 [a] | 68.5 ± 0.8 [a] | 68.0 ± 0.7 [a] |
| Initial % Fat | 6.8 ± 0.8 [a] | 5.3 ± 0.6 [a] | 5.6 ± 0.6 [a] |
| Final Body Wt (g) | 42.3 ± 0.7 [a] | 40.8 ± 0.5 [a] | 36.6 ± 0.9 [b] |
| Final Lean Mass (g) | 20.9 ± 0.3 [a] | 20.6 ± 0.3 [a] | 20.9 ± 0.7 [a] |
| Final Fat Mass (g) | 17.3 ± 0.8 [a] | 16.3 ± 0.3 [a] | 11.6 ± 1.2 [b] |
| Final % Lean | 49.6 ± 1.0 [a] | 50.4 ± 0.5 [a] | 57.3 ± 2.1 [b] |
| Final % Fat | 40.9 ± 1.5 [a] | 39.8 ± 0.7 [a] | 31.4 ± 2.8 [b] |
| Retroperitoneal Fat Pad Wt (mg) | 1041.0 ± 57.7 [a] | 986.1 ± 21.8 [a] | 709.8 ± 72.2 [b] |
| Epididymal Fat Pad Wt (mg) | 2449.9 ± 90.0 [a] | 2208.6 ± 52.0 [a] | 1713.8 ± 139.8 [b] |
| Skeletal Muscle Wt (mg/g Final Body Wt) | 24.8 ± 0.6 [a] | 25.5 ± 0.4 [a] | 29.1 ± 1.0 [b] |

Figure 4:
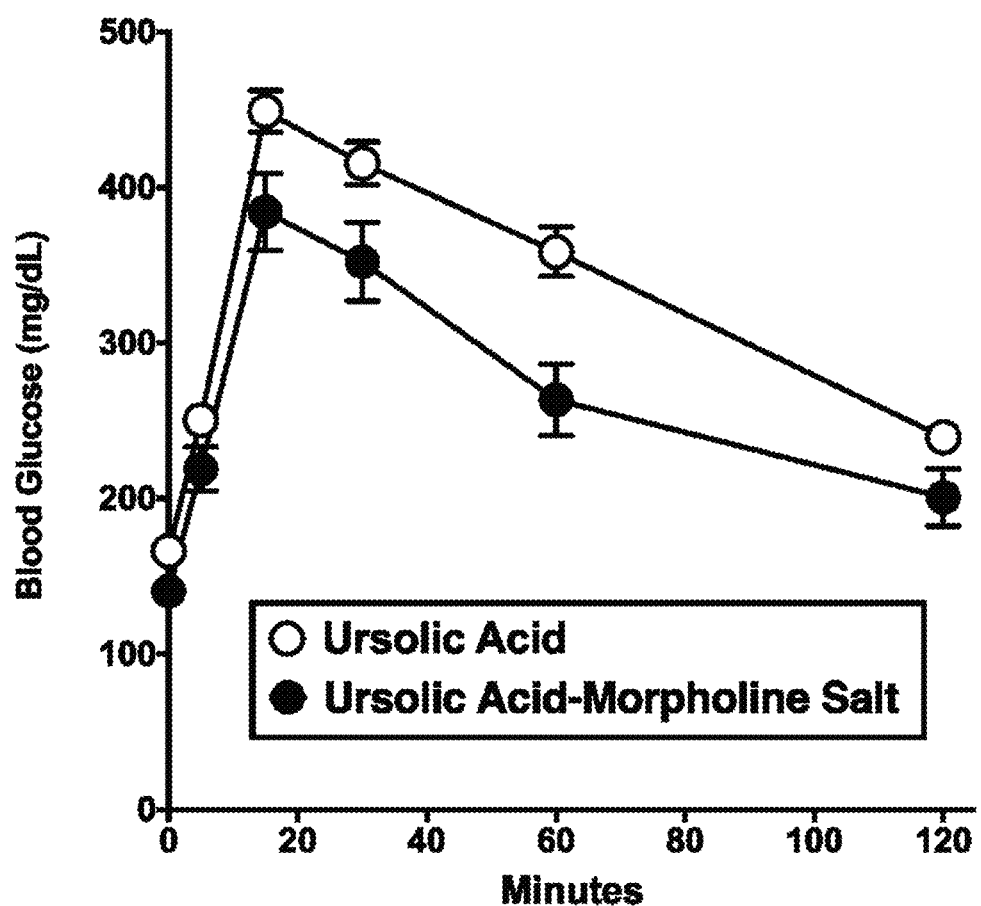
FIG. 4 is a graph depicting glucose tolerance testing results.

Direct Comparison of Ursolic Acid-Morpholine Salt to a Molar-Matched Dose of Ursolic Acid in Obesity-Induced Glucose Intolerance Weight-matched cohorts of 8-week old male C57BL/6 mice were randomized to receive ad libitum access to either high-fat chow supplemented with 0.050% ursolic acid, or high-fat chow supplemented with a molar-matched dose of ursolic acid-morpholine salt (0.059%). After mice had consumed the diets for 7 weeks, mice were fasted for 6 hours and then subjected to glucose tolerance testing. Results are shown in FIG. 4, which is a graph depicting glucose tolerance testing results. Data are means±SEM from 10 mice per cohort. The fasting blood glucose for mice treated with ursolic acid-morpholine salt (140.6±7.8 mg/dL) is significantly lower than the fasting blood glucose for mice treated with ursolic acid (166.3±3.7; P<0.01). In addition, the area under the curve (AUC) for mice treated with ursolic acid-morpholine salt (32,606±2,471) is significantly lower than the AUC for mice treated with ursolic acid (40,585±1,357; P<0.01), indicating that ursolic acid-morpholine salt significantly reduced glucose intolerance relative to a molar-matched dose of ursolic acid.

Figure 5:
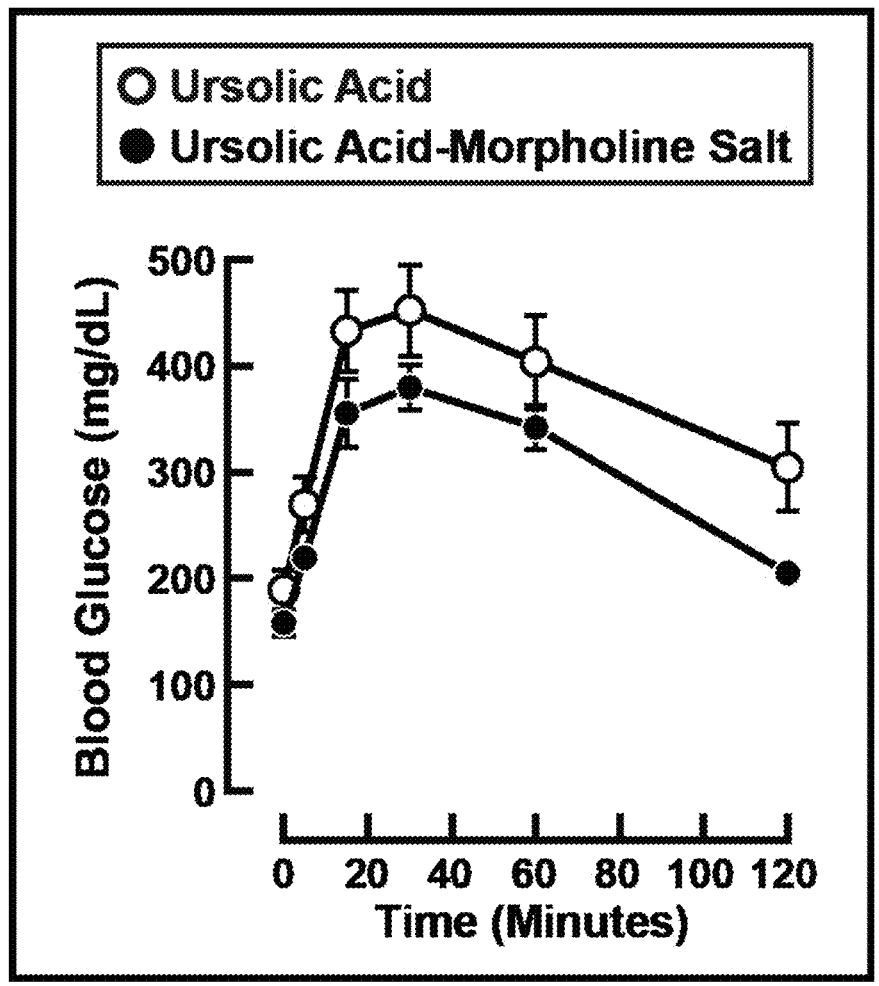
FIG. 5 is a graph depicting glucose tolerance testing results.

Ursolic Acid-Morpholine Salt is More Efficacious than a Maximally Effective Dose of Ursolic Acid As an additional side-by-side comparison, testing was undertaken whereby mice were provided ad lib access to high-fat diet containing either 0.059% ursolic acid-morpholine salt or a >3-fold higher, maximally effective dose of ursolic acid (0.20% w/w; see Kunkel et al., Ursolic acid increases skeletal muscle and brown fat and decreases diet-induced obesity, glucose intolerance and fatty liver disease, *PLOS One* 7, (2012) e39332; Kunkel et al., mRNA expression signatures of human skeletal muscle atrophy identify a natural compound that increases muscle mass, *Cell Metabolism* 13, (2011) 627-638). Specifically, weight-matched cohorts of 8-wk-old male C57BL/6 mice were randomized to receive ad libitum access to high-fat diet containing either a maximally effective dose of ursolic acid (0.20% w/w) or 0.059% (w/w) ursolic acid-morpholine salt. After 7 weeks on the diets, mice were fasted for 6 hours and were then subjected to glucose tolerance tests. Results are shown in FIG. 5, which is a graph depicting glucose tolerance testing results. Data are means±SEM from 8 mice/diet. The area under the curve (AUC) for ursolic acid-morpholine salt is significantly lower than the AUC for ursolic acid (P<0.05). Relative to the greater than 3-fold higher, maximally effective dose of ursolic acid, ursolic acid-morpholine salt significantly improved glucose tolerance (FIG. 5) as well as other parameters including grip strength (P=0.05). These data provide further evidence that ursolic acid-morpholine salt is significantly more potent and significantly more efficacious than ursolic acid.

Figure 6:
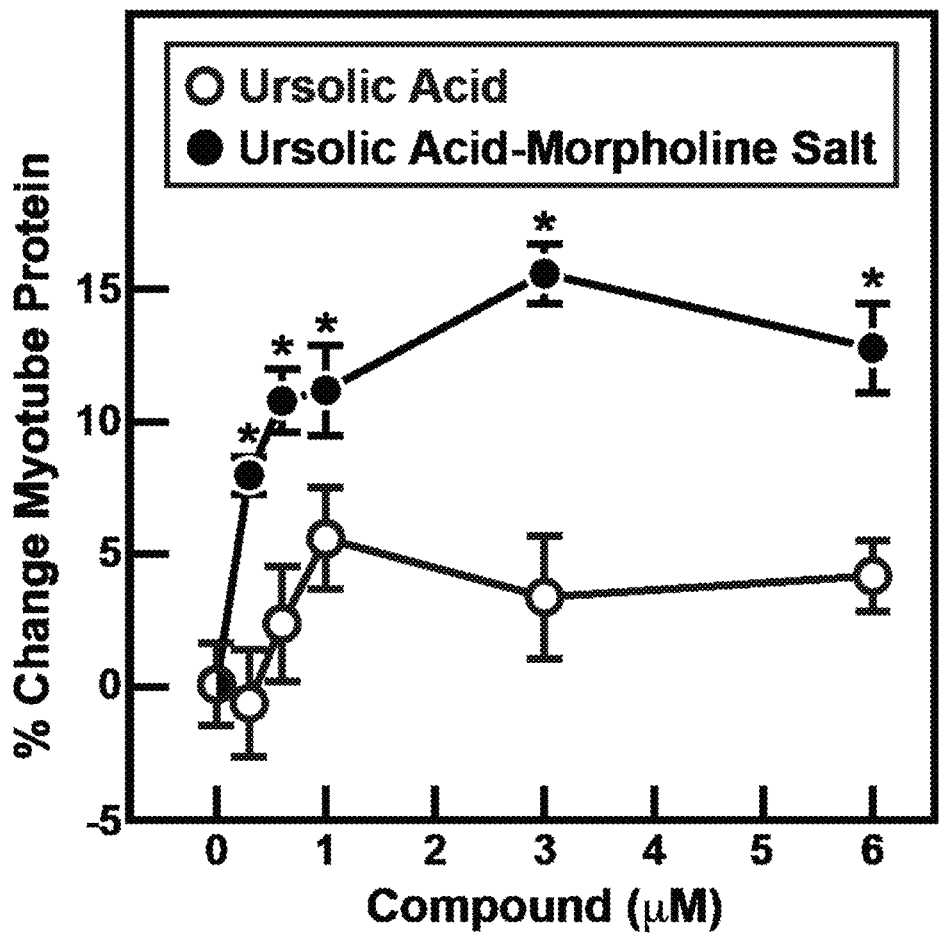
FIG. 6 is a graph depicting testing results for percent change in total cellular protein.

Ursolic Acid-Morpholine Salt is More Efficacious and More Potent than Ursolic Acid A direct, side-by-side comparison of ursolic acid and ursolic acid-morpholine salt was performed in an in vitro model of skeletal muscle. C2C12 myoblasts were cultured and fully differentiated into post-mitotic skeletal myotubes, then incubated for 48 hours with 10% fetal bovine serum (FBS) plus the indicated concentrations of ursolic acid or ursolic acid-morpholine salt. Myotubes were then harvested for assessment of total cellular protein, which increases as myotubes undergo hypertrophy. (See Dyle et al., Systems-based discovery of tomatidine as a natural small molecule inhibitor of skeletal muscle atrophy, *Journal of Biological Chemistry* 289, (2014) 14913-14924.) Total protein in each sample was normalized to the amount of in vehicle-treated myotubes. Each data point represents the mean±SEM of ≥5 samples. *P<0.05 relative to the equivalent dose of ursolic acid. Results are shown in FIG. 6, which is a graph depicting results from the direct, side-by-side comparison of ursolic acid and ursolic acid-morpholine salt in the cultured C2C12 myotubes in vitro model of skeletal muscle. As shown, both ursolic acid and ursolic acid-morpholine salt significantly increased total cellular protein in a dose-dependent manner, consistent with their capacity to induce myotube hypertrophy. However, ursolic acid-morpholine salt was 3-fold more efficacious and 3-fold more potent than ursolic acid.

As used herein, the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or composition that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A method for:
(i) increasing skeletal muscle mass;
(ii) treating skeletal muscle atrophy;
(iii) reducing muscle atrophy;
(iv) treating sarcopenia;
(v) treating cachexia;
(vi) increasing strength;
(vii) treating weakness;
(viii) reducing weakness;
(ix) increasing exercise capacity;
(x) promoting muscle growth;
(xi) increasing the ratio of skeletal muscle to fat;
(xii) reducing fat;
(xiii) treating obesity;
(xiv) treating diabetes;
(xv) lowering blood glucose;
(xvi) treating pre-diabetes;
(xvii) treating metabolic syndrome; or
(xviii) treating insulin resistance;
in a subject in need thereof, the method comprising administering to the subject an effective amount of an ursolic acid salt selected from ursolic acid diethanolamine salt and ursolic acid morpholine salt.

2. The method according to claim 1, wherein the salt is ursolic acid diethanolamine salt of formula

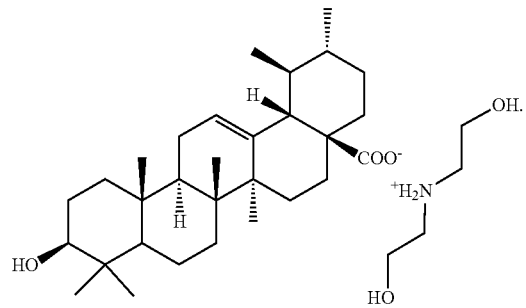

3. The method according to claim 1, wherein the salt is ursolic acid morpholine salt of formula

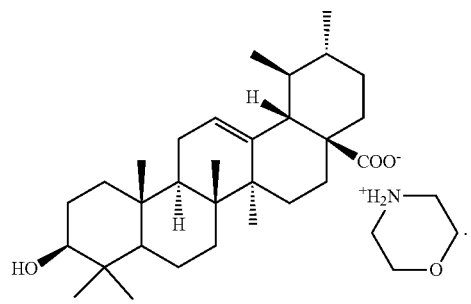

4. The method according to claim 1, comprising administering to the subject 25 to 1,500 mg of the salt.

5. The method according to claim 4, wherein the salt is ursolic acid diethanolamine salt of formula

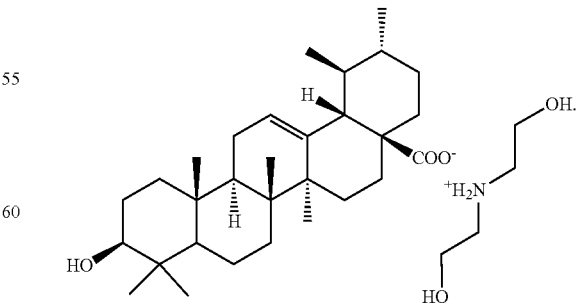

6. The method according to claim 1, wherein the salt is ursolic acid morpholine salt of formula

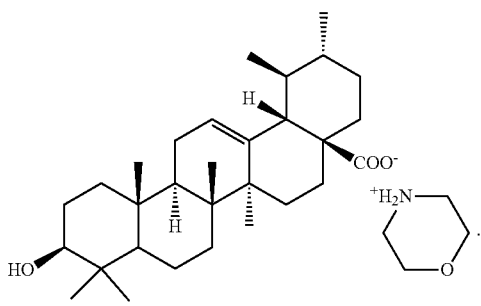

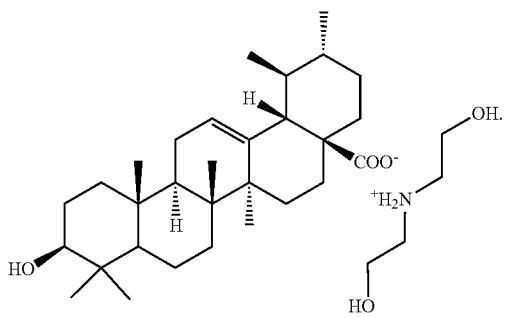

7. The method according to claim 1, wherein the subject is a human, non-human primate, horse, pig, rabbit, dog, sheep, goat, cow, cat, guinea pig, hamster, ferret, fish, bird, or rodent.

8. The method according to claim 7, wherein the salt is ursolic acid diethanolamine salt of formula

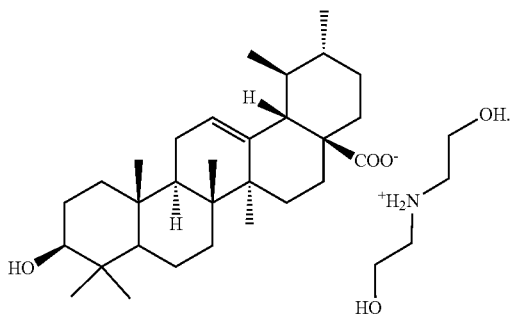

9. The method according to claim 7, wherein the salt is ursolic acid morpholine salt of formula

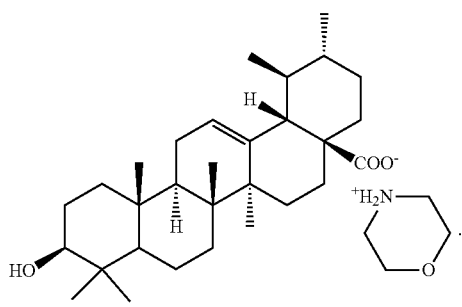

10. The method according to claim 1, comprising administering a composition comprising the salt and a further agent.

11. The method according to claim 10, wherein the composition comprises 25 to 1,500 mg of the salt.

12. The method according to claim 11, wherein the salt is ursolic acid diethanolamine salt of formula 13. The method according to claim 11, wherein the salt is ursolic acid morpholine salt of formula

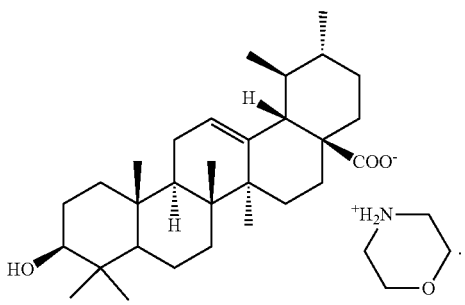

14. The method according to claim 10, wherein the composition comprises 50 to 1,000 mg of the salt.

15. The method according to claim 10, wherein the composition is a pharmaceutical composition, nutraceutical composition, food composition, or dietary supplement.

16. The method according to claim 15, wherein the salt is ursolic acid morpholine salt of formula

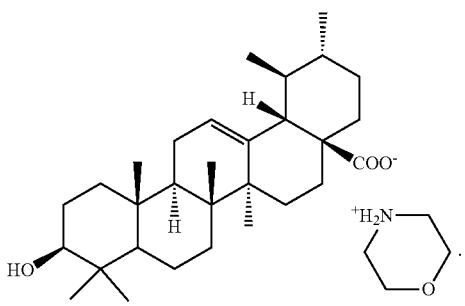

17. The method according to claim 3, for increasing skeletal muscle mass.

18. The method according to claim 3, for treating skeletal muscle atrophy.

19. The method according to claim 3, for treating sarcopenia.

20. The method according to claim 3, for treating cachexia.

21. The method according to claim 3, for increasing strength.

22. The method according to claim 3, for treating weakness.

23. The method according to claim 3, for increasing exercise capacity.

24. The method according to claim 3, for promoting muscle growth.

25. The method according to claim 3, for increasing the ratio of skeletal muscle to fat.

26. The method according to claim 3, for reducing fat.

27. The method according to claim 3, for treating obesity.

28. The method according to claim 3, for treating diabetes.

29. The method according to claim 3, for lowering blood glucose.

30. The method according to claim 3, for treating pre-diabetes.

31. The method according to claim 3, for treating metabolic syndrome.

32. The method according to claim 3, for treating insulin resistance.

33. The method according to claim 3, for reducing muscle atrophy.

34. The method according to claim 3, for reducing weakness.

\* \* \* \* \*